(12) United States Patent
Tsutsumi et al.

(10) Patent No.: US 11,669,084 B2
(45) Date of Patent: Jun. 6, 2023

(54) CONTROLLER AND CONTROL SYSTEM

(71) Applicant: Fanuc Corporation, Yamanashi (JP)

(72) Inventors: Kentarou Tsutsumi, Yamanashi (JP); Yasushi Hayashi, Yamanashi (JP)

(73) Assignee: Fanuc Corporation, Yamanashi (JP)

( * ) Notice: Subject to any disclaimer, the term of this patent is extended or adjusted under 35 U.S.C. 154(b) by 155 days.

(21) Appl. No.: 17/038,239

(22) Filed: Sep. 30, 2020

(65) Prior Publication Data
US 2021/0116906 A1    Apr. 22, 2021

(30) Foreign Application Priority Data

Oct. 16, 2019  (JP) .............................. JP2019-189438

(51) Int. Cl.
| G05B 23/02 | (2006.01) |
| G05B 19/418 | (2006.01) |
| G06F 1/16 | (2006.01) |
| G06T 7/00 | (2017.01) |

(52) U.S. Cl.
CPC ..... *G05B 23/0291* (2013.01); *G05B 19/4183* (2013.01); *G05B 19/4185* (2013.01); *G05B 19/41875* (2013.01); *G06F 1/163* (2013.01); *G06T 7/0012* (2013.01)

(58) Field of Classification Search
CPC ............ G05B 23/0291; G05B 19/4183; G05B 19/4185; G05B 19/41875; G05B 9/02; G05B 19/0428; G05B 2219/24162; G06F 1/163; G06T 7/0012; A61B 5/0002; A61B 5/0205; A61B 5/6801
See application file for complete search history.

(56) References Cited

U.S. PATENT DOCUMENTS

| 2017/0157783 A1* | 6/2017 | Ogawa ..................... F16P 3/003 |
| 2017/0197313 A1* | 7/2017 | Nishino ............. A61B 5/02055 |
| 2017/0255193 A1* | 9/2017 | Berg ..................... G05B 19/048 |
| 2019/0179286 A1* | 6/2019 | Horseman .............. A61B 5/369 |

FOREIGN PATENT DOCUMENTS

| JP | 2012212349 A | 11/2012 |
| JP | 2018038604 A | 3/2018 |

OTHER PUBLICATIONS

P. Li, R. Meziane, M. J.—. Otis, H. Ezzaidi and P. Cardou, "A Smart Safety Helmet using IMU and EEG sensors for worker fatigue detection," 2014 IEEE International Symposium on Robotic and Sensors Environments (ROSE) Proceedings, 2014, pp. 55-60, doi: 10.1109/ROSE.2014.6952983. (Year: 2014).*

* cited by examiner

*Primary Examiner* — Christopher E. Everett
(74) *Attorney, Agent, or Firm* — RatnerPrestia

(57) ABSTRACT

A controller acquires biometric information of a worker and environmental information related to work environment and determines a safety level of the worker in a plurality of steps according to a safety level determination condition stored in advance on the basis of the acquired biometric information and environmental information. Then, the controller continuously controls an operation of an industrial machine in a state of a predetermined restriction being applied to a driving unit of the industrial machine and in a state of a predetermined safety function being activated on the basis of the determined safety level.

3 Claims, 7 Drawing Sheets

FIG. 5

| WORKER IDENTIFICATION INFORMATION | NAME | EMPLOYEE NUMBER | AGE | GENDER | MACHINE 1 MANAGEMENT | MACHINE 1 DRIVING | MACHINE 1 PARAMETER CHANGING | ... |
|---|---|---|---|---|---|---|---|---|
| 1000 | X | 900012 | 48 | MALE | ○ | AVAILABLE | AVAILABLE | ... |
| 0002 | Y | 010538 | 40 | FEMALE | × | AVAILABLE | AVAILABLE | ... |
| 0248 | Z | 115410 | 25 | MALE | × | AVAILABLE | UNAVAILABLE | ... |
| 1163 | T | 826003 | 62 | FEMALE | × | UNAVAILABLE | AVAILABLE | ... |
| ... | ... | ... | ... | ... | ... | ... | ... | ... |

FIG. 7

| SAFETY LEVEL | BODY TEMPERATURE | BLOOD PRESSURE | HEART RATE | TEMPERATURE | HUMIDITY | ... |
|---|---|---|---|---|---|---|
| 5 (NORMAL) | ~36.5°C | ... | ... | ... | ... | ... |
| 4 (CONFIRMED) | 36.5°C~37.0°C | ... | ... | ... | ... | ... |
| 3 (ALERT) | 37.0°C~37.5°C | ... | ... | ... | ... | ... |
| 2 (MANIPULATION RESTRICTION) | 37.5°C~38.0°C | ... | ... | ... | ... | ... |
| 1 (WORK STOP) | 38.0°C~ | ... | ... | ... | ... | ... |

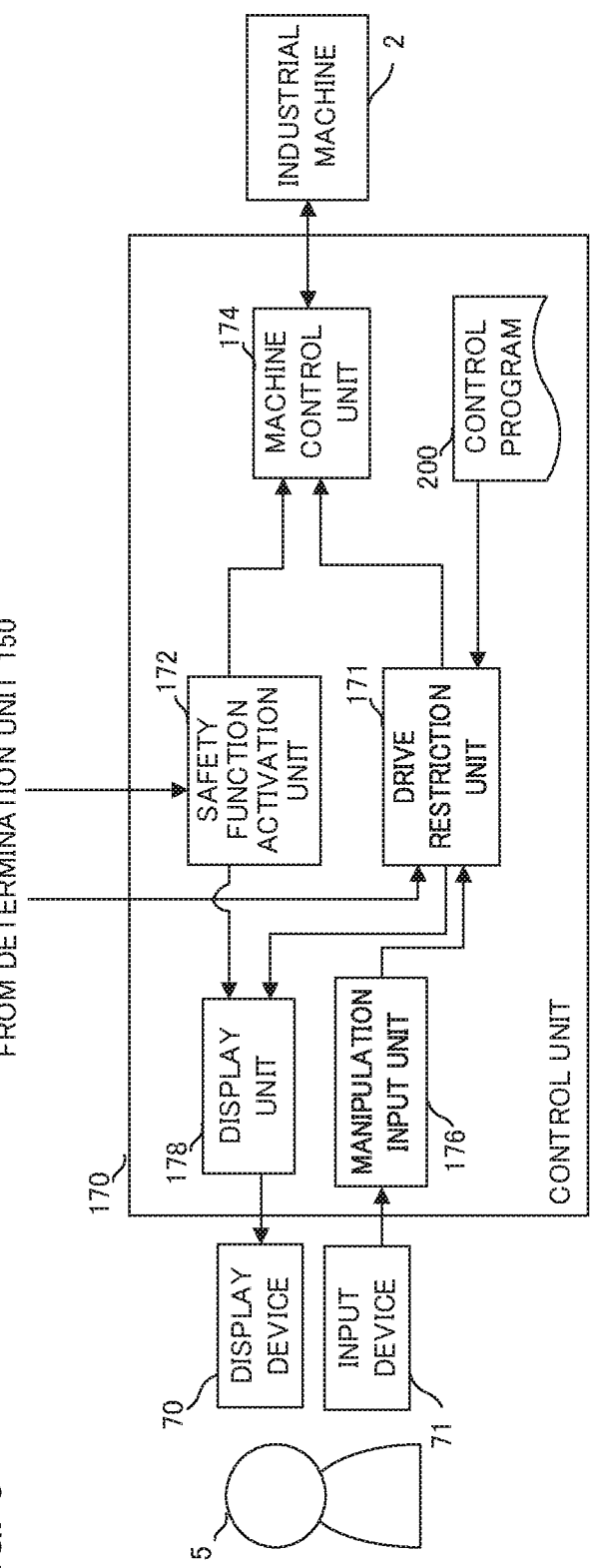

CONTROLLER AND CONTROL SYSTEM

RELATED APPLICATIONS

The present application claims priority to Japanese Patent Application Number 2019-189438 filed on Oct. 16, 2019, the disclosure of which is hereby incorporated by reference herein in its entirety.

BACKGROUND OF THE INVENTION

1. Field of the Invention

The application relates to a controller and a control system.

2. Description of the Related Art

Many industrial machines are installed at manufacturing sites such as factories. At the manufacturing sites, workers perform manufacturing work by manipulating respective industrial machines. There is known a technique in which an ID or the like is assigned to the worker and authentication is performed during the work for the purpose of managing the work of the workers at the manufacturing sites (refer to JP 2012-212349 A, or the like).

In the management of the worker at the manufacturing site, a physical condition of the worker is managed, and in a case where the physical condition is poor, the work performed by the worker may be restricted. For example, there is known a system that monitors biometric information of the worker and safely stops an industrial machine in a case where a physical abnormality is recognized (refer to JP 2018-038604 A, or the like).

In an actual work at the manufacturing sites, there is a risk of causing an erroneous manipulation due to a change in physical condition of the worker. Furthermore, a degree of the attention and concentration of the worker is reduced depending on environmental conditions such as a temperature, and there is a possibility of an erroneous manipulation associated with the reduction of the degree of the attention and concentration. Therefore, a state of the worker and an environmental state are also taken into consideration during actually working of the worker, in a case where a danger is expected, the work is restricted.

At the manufacturing sites, if an operation of the industrial machine is stopped in order to impose a restriction on the work, the production efficiency of a product will be suddenly decreased. If the production efficiency of the product is suddenly decreased, not only the work in charge but all related work will be affected, and thus, it does not intend to stop the operation of the industrial machine. On the other hand, in some cases, depending on the state of the worker and the environmental state, the work may not be stopped and may be continued while considering the safety. In view of these situations, it is preferable to continuously produce the product and to ensure the safety of the work of the worker while taking into consideration the state of the worker and the environmental state.

SUMMARY OF THE INVENTION

Therefore, it is preferable to reduce the risk of manipulation error and accident occurrence from a machine side while monitoring a state of a worker and an environmental state.

A controller and a control system according to an aspect of the application monitor a state of a worker and an environmental state and determine a safety level of the worker according to contents of monitoring. Then, partial work restriction on work of the worker and activation of the safety function are controlled according to the determined safety level.

According to an aspect of the application, there is provided a controller controlling an industrial machine, the controller including: a biometric information acquisition unit acquiring biometric information of a worker; an environmental information acquisition unit acquiring environmental information related to work environment of the worker; a determination condition storage unit storing a safety level determination condition as a condition for determining a safety level of the worker in a plurality of steps on the basis of the biometric information and the environmental information; a safety level determination unit determining the safety level of the worker according to the safety level determination condition stored in the determination condition storage unit on the basis of the biometric information acquired by the biometric information acquisition unit and the environmental information acquired by the environmental information acquisition unit; a drive restriction unit continuing the operation of the industrial machine in a state of a predetermined restriction being applied to a driving unit of the industrial machine on the basis of the safety level determined by the safety level determination unit; and a safety function activation unit continuing the operation of the industrial machine in a state of a predetermined safety function being activated on the basis of the safety level determined by the safety level determination unit.

According to another aspect of the application, there is provided a control system configured by connecting a controller controlling an industrial machine and a computer via a network, the control system comprising: a biometric information acquisition unit acquiring biometric information of a worker; an environmental information acquisition unit acquiring environmental information related to work environment of the worker; a determination condition storage unit storing a safety level determination condition as a condition for determining a safety level of the worker on the basis of the biometric information and the environmental information; a safety level determination unit determining the safety level of the worker according to the safety level determination condition stored in the determination condition storage unit on the basis of the biometric information acquired by the biometric information acquisition unit and the environmental information acquired by the environmental information acquisition unit; a drive restriction unit continuing the operation of the industrial machine in a state of a predetermined restriction being applied to a driving unit of the industrial machine on the basis of the safety level determined by the safety level determination unit; and a safety function activation unit continuing the operation of the industrial machine in a state of a predetermined safety function being activated on the basis of the safety level determined by the safety level determination unit.

According to an aspect of the application, work can be continued without suddenly lowering the production efficiency of the industrial machine and with actively reducing the risk of manipulation error or accident occurrence.

BRIEF DESCRIPTION OF THE DRAWINGS

The above and other objects and features of the application will be apparent from the following description of embodiments with reference to the accompanying drawings. Of the drawings:

FIG. 5 is a diagram illustrating an example of worker information;

FIG. 7 is a diagram illustrating an example of safety level determination conditions;

FIG. 8 is a block diagram illustrating a schematic function of a control unit;

FIG. 9 is a diagram illustrating an example of a drive restriction and safety function being activated according to a safety level.

DETAILED DESCRIPTION OF THE PREFERRED EMBODIMENTS

Hereinafter, embodiments will be described with reference to the drawings.

Figure 1:
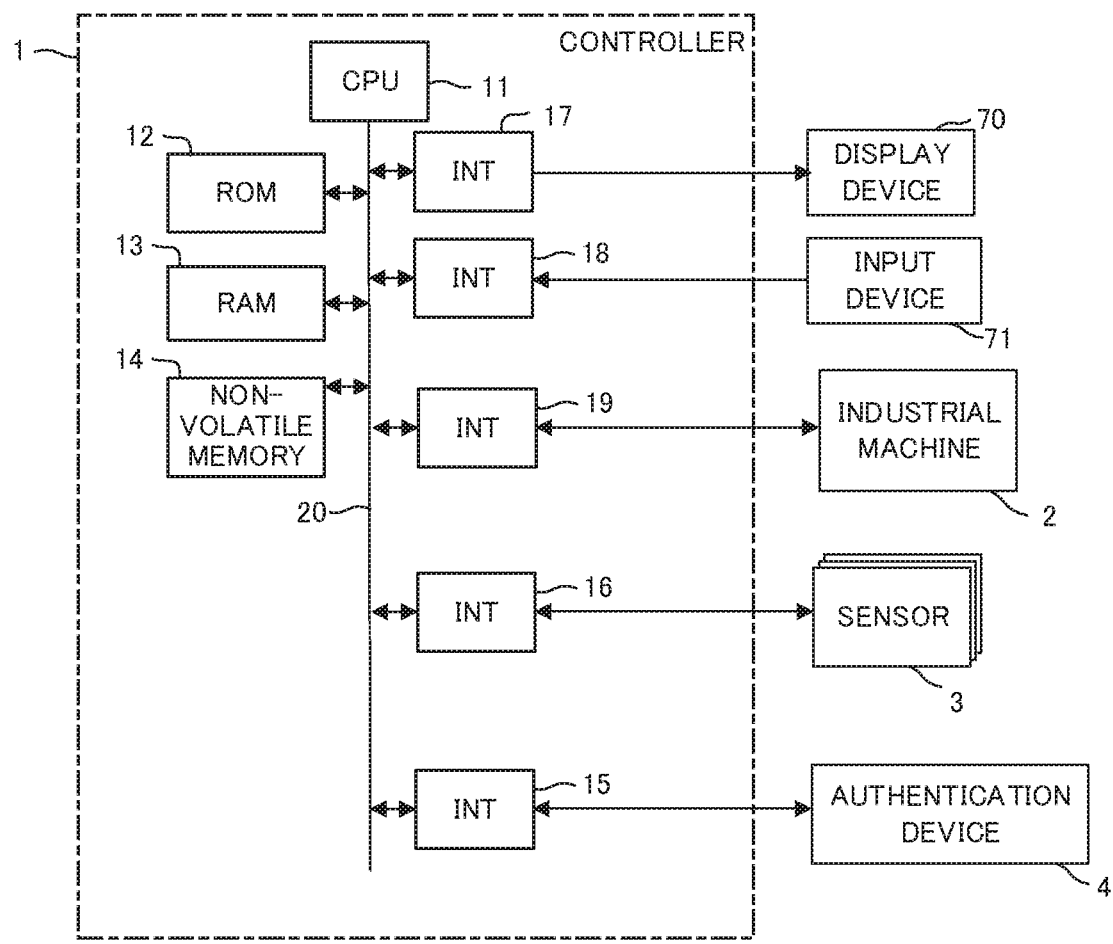
FIG. 1 is a schematic hardware configuration diagram of a controller according to a first embodiment.

FIG. 1 is a schematic hardware configuration diagram illustrating main units of a controller according to a first embodiment. The controller 1 can be mounted on, for example, a controller that controls an industrial machine.

A CPU 11 included in the controller 1 according to the embodiment is a processor that controls the controller 1 as a whole. The CPU 11 reads out a system program stored in a ROM 12 via a bus 20. The CPU 11 controls the entire controller 1 according to the read system program. Calculation data, display data, various data input from the outside, and the like are temporarily stored in a RAM 13.

A non-volatile memory 14 is configured with, for example, a memory backed up by a battery (not illustrated), a solid state drive (SSD), or the like. The non-volatile memory 14 retains a storage state even though the controller 1 is powered off. The non-volatile memory 14 stores a control program input via an input device 71, data acquired from an industrial machine 2 or the like via an interface 19, data acquired from a sensor 3 via an interface 16, and the like. The control program and various data stored in the non-volatile memory 14 may be loaded in the RAM 13 at the time of execution/use. In addition, various system programs such as a known analysis program are written in the ROM 12 in advance.

Each data read on the memory, data obtained as a result of execution of a program, or the like, data acquired from the industrial machine, or the like are output via an interface 17 and displayed on a display device 70. The input device 71 including a keyboard, a pointing device, and the like receives a command, data, and the like on the basis of a manipulation by a worker and transfers the command and data to the CPU 11 via an interface 18.

The controller 1 is connected to the industrial machine 2 via the interface 19. The controller 1 drives a driving unit such as a motor included in the industrial machine 2 according to the control program to control the position, speed, and the like of a shaft included in the industrial machine 2. In addition, the controller 1 acquires the position, speed, acceleration of the shaft included in the industrial machine 2, the current value and voltage value of a driving unit such as a motor included in the industrial machine 2, and the detection value and the like detected by a sensor (not illustrated) installed in the industrial machine 2. The controller 1 can store the acquired data in the RAM 13 or the non-volatile memory 14 in association with the time point and the like.

The controller 1 is connected to one or a plurality of the sensors 3 via the interface 16. The sensor 3 is installed, for example, in the vicinity of the controller 1 and the industrial machine 2 and detects biometric information of the worker who is working by using the controller 1 and the industrial machine 2. The sensor 3 may detect the biometric information of the worker 5 at the work site from the outside. For example, if the work site is imaged by using thermography as the sensor 3, the body temperature of the worker 5 can be detected. The complexion and behavior (change in movement, shaking of hands, or the like) of the worker 5 may be allowed to be detected by using an imaging device of a camera or the like as the sensor 3. In addition, the sensor 3 may be attached to the worker to detect the biometric information of the worker. In a case where such a configuration is employed, the interface 16 is configured as, for example, a short-range wireless communication interface. Then, the worker 5 wears a blood pressure meter, a heart rate monitor, a blood oxygen concentration meter, or the like as the sensor 3 and carries a short-range wireless terminal connected to the sensor 3. When the worker 5 enters the work site, the short-range wireless terminal carried by the worker 5 enters a wireless communication state with the short-range wireless communication interface as the interface 16, so that the CPU 11 can acquire the biometric information of the worker detected by the sensor 3. In addition, the sensor 3 may detect environmental information such as temperature and humidity, for example, in the vicinity of the controller 1 and the industrial machine 2. The controller 1 can store the data acquired from the sensor 3 in the non-volatile memory 14 in association with the time point and the like.

The controller 1 is connected to an authentication device 4 via the interface 15. The controller 1 authenticates the worker who is using the industrial machine 2 on the basis of the information for identifying the worker acquired via the authentication device 4. The authentication device 4 may be, for example, an IC card reader that authenticates the worker with an IC card carried by the worker or a sensor device that detects an ID badge or an identification code worn by the worker. In addition, the authentication device 4 may be a fingerprint authentication device, an iris authentication device, or the like that authenticates the worker on the basis of biometric information such as a fingerprint or iris of the worker. The controller 1 can store the acquired authentication information of the worker in the non-volatile memory 14 in association with the time point and the like. In addition, the authentication device 4 is not necessarily provided in the case of using a configuration in which the worker is authenticated by allowing the worker to input identification information by using the display device 70 and the input device 71. In a case where such a configuration is employed, the display device 70 and the input device 71 play the role of the authentication device 4.

Figure 2:
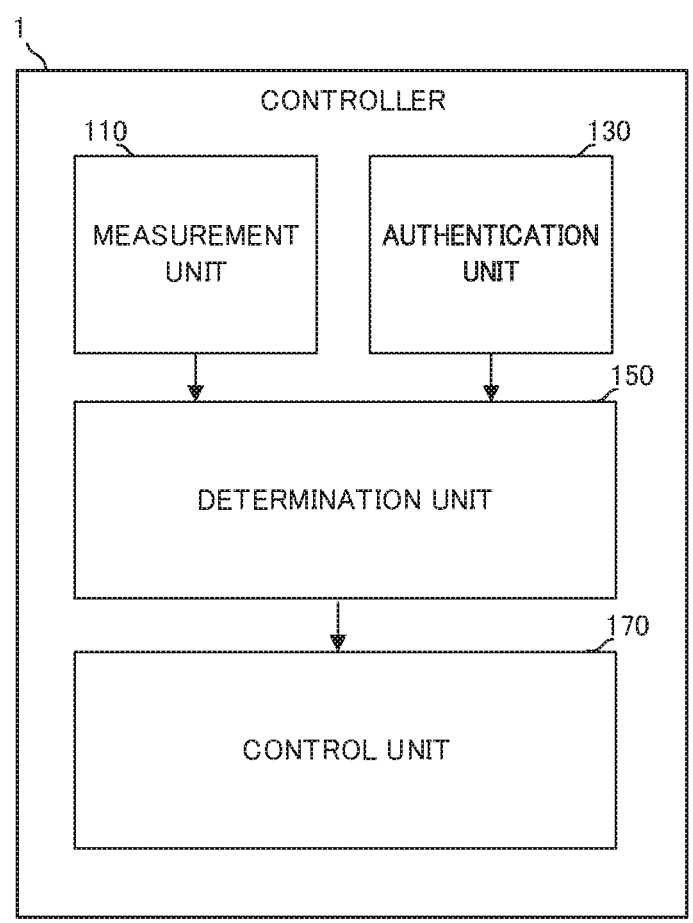
FIG. 2 is a block diagram illustrating a schematic function of the controller according to the first embodiment.

FIG. 2 is a block diagram illustrating a schematic function of the controller 1 according to the first embodiment. Each function illustrated in FIG. 2 is realized by the CPU 11 included in the controller 1 illustrated in FIG. 1 executing the system program and controlling the operation of each unit of the controller 1.

The controller 1 according to the embodiment includes a measurement unit 110, an authentication unit 130, a determination unit 150, and a control unit 170.

The measurement unit 110 executes the system program read from the ROM 12 by the CPU 11 included in the controller 1 illustrated in FIG. 1 and mainly performs arithmetic processing using the RAM 13 and the non-volatile memory 14, input/output processing using the interface 16, and the like by the CPU 11. The measurement unit 110 measures the biometric information of the worker measured by the sensor 3.

Figure 3:
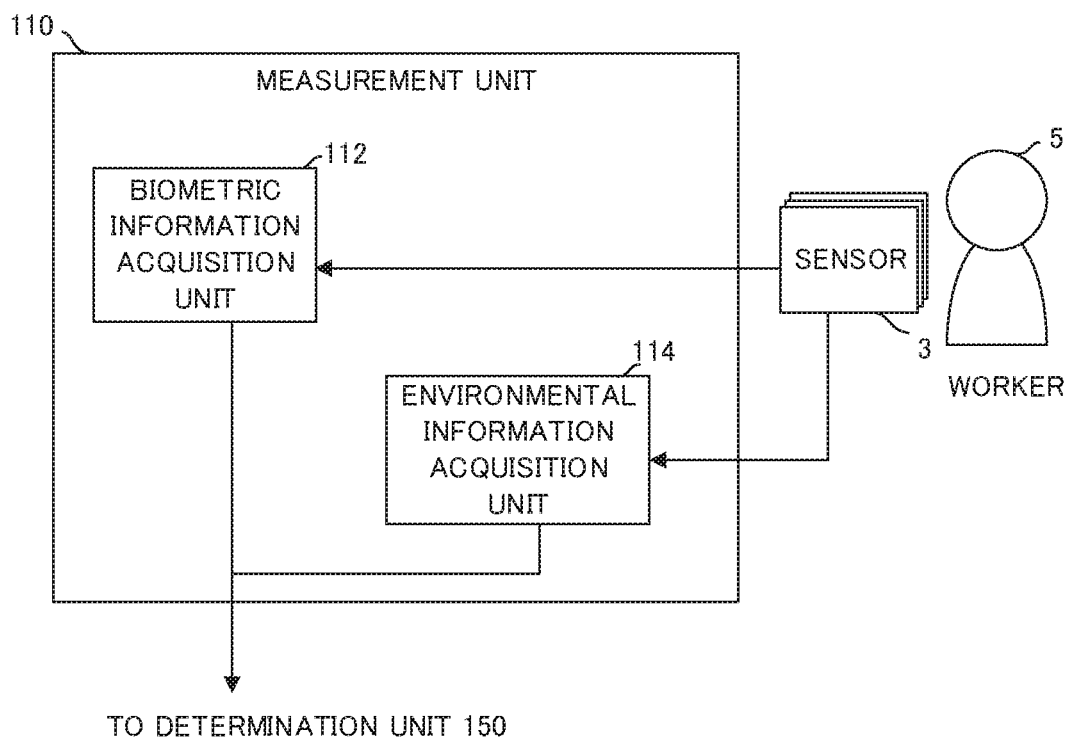
FIG. 3 is a block diagram illustrating a schematic function of a measurement unit.

FIG. 3 is a block diagram illustrating a schematic function of the measurement unit 110 according to the embodiment. The measurement unit 110 includes a biometric information acquisition unit 112 and an environmental information acquisition unit 114. The biometric information acquisition unit 112 acquires the biometric information of the worker 5 measured by the sensor 3 and outputs the biometric information to the determination unit 150. It is preferable that the biometric information of the worker 5 acquired by the biometric information acquisition unit 112 can be used for estimating the physical condition of the worker 5, such as a body temperature, a blood pressure, a heart rate, a respiration rate, a blood oxygen concentration, and complexion of the worker 5.

The environmental information acquisition unit 114 acquires environmental information related to the work environment of the worker 5 measured by the sensor 3 and outputs the environmental information to the determination unit 150. It is preferable that the environmental information acquired by the environmental information acquisition unit 114 is assumed to affect the physical condition of the worker 5, such as the temperature and humidity of the work environment, the oxygen and carbon dioxide components in the air, and the concentration of cutting fluid mist.

The authentication unit 130 executes the system program read from the ROM 12 by the CPU 11 included in the controller 1 illustrated in FIG. 1 and mainly performs arithmetic processing using the RAM 13 and the non-volatile memory 14, input/output processing using the interface 15, and the like by the CPU 11. The authentication unit 130 controls the authentication device 4 to authenticate the worker.

Figure 4:
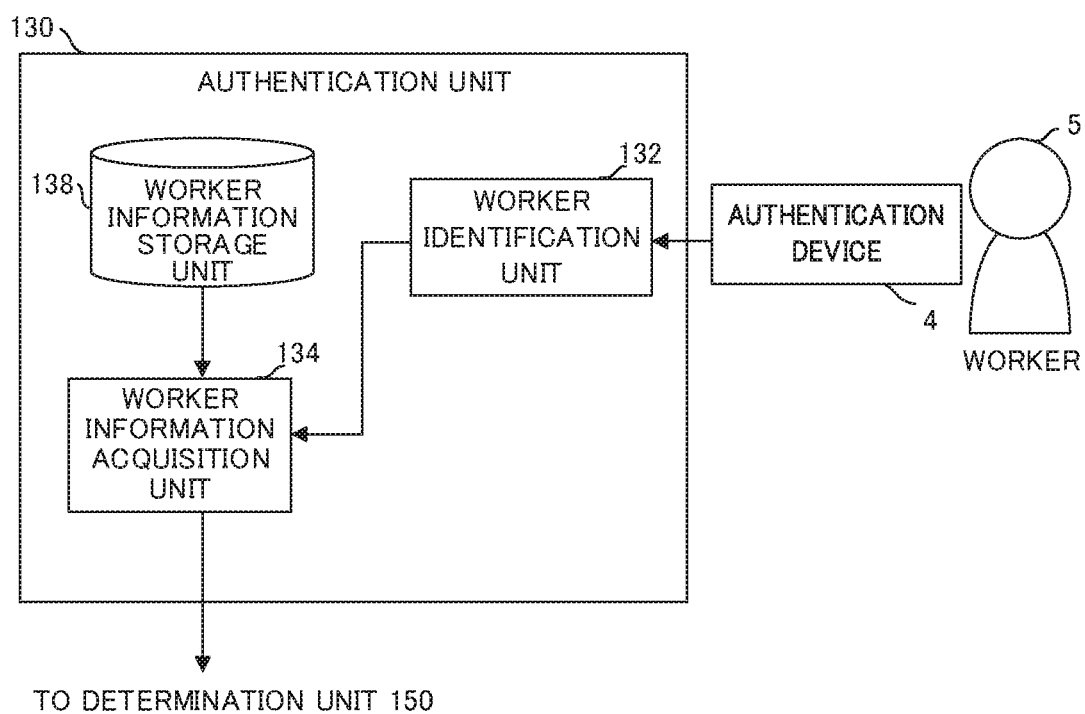
FIG. 4 is a block diagram illustrating a schematic function of an authentication unit.

FIG. 4 is a block diagram illustrating a schematic function of the authentication unit 130 according to the embodiment. The authentication unit 130 includes a worker identification unit 132, a worker information acquisition unit 134, and a worker information storage unit 138.

The worker identification unit 132 acquires information (worker identification information) required for identifying the worker via the authentication device 4. It is preferable that the worker identification information acquired by the worker identification unit 132 is information that can uniquely identify the worker 5 who performs work at the manufacturing site. As an example, the worker identification information may be an ID of an IC card carried by the worker 5 and used for authentication. As another example, the worker identification information may be information indicating a physical characteristic of the worker 5, such as a fingerprint or an iris. In addition, the worker identification information may be an ID input from the input device 71 that operates as the authentication device 4. The worker identification unit 132 outputs the worker identification information acquired from the authentication device 4 to the worker information acquisition unit 134.

The worker information acquisition unit 134 reads the worker information stored in the worker information storage unit 138 on the basis of the worker identification information input from the worker identification unit 132 and outputs the worker information to the determination unit 150. The worker information storage unit 138 stores the worker information about a plurality of the workers 5 who perform work at the manufacturing site in advance.

FIG. 5 is a diagram illustrating an example of the worker information stored in the worker information storage unit 138. The worker information is defined as information used for managing the worker associated with the worker identification information. The worker information may include, for example, the name, employee number, and the like of worker. The worker information may be associated with the age, gender, and other attributes of worker. The worker information may include manipulation availability information including a management authority, a driving authority, a parameter changing authority, and the like of the worker related to the industrial machine 2 controlled by the controller 1.

The determination unit 150 executes the system program read from the ROM 12 by the CPU 11 included in the controller 1 illustrated in FIG. 1 and mainly performs arithmetic processing using the RAM 13 and the non-volatile memory 14 by the CPU 11. The determination unit 150 determines a safety level of the worker on the basis of the worker information of the worker authenticated by the authentication unit 130 and the biometric information and the environmental information of the worker measured by the measurement unit 110.

Figure 6:
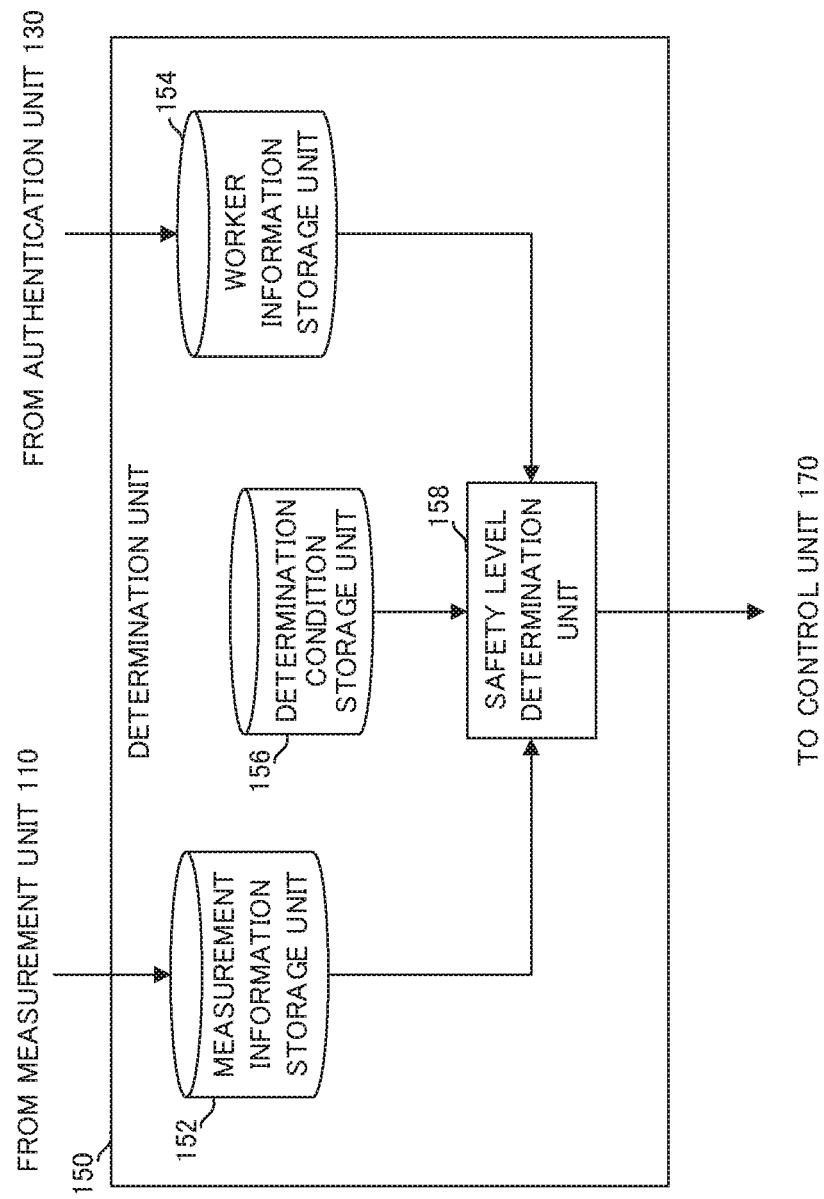
FIG. 6 is a block diagram illustrating a schematic function of a determination unit.

FIG. 6 is a block diagram illustrating a schematic function of the determination unit 150 according to the embodiment. The determination unit 150 includes a measurement information storage unit 152, a worker information storage unit 154, a determination condition storage unit 156, and a safety level determination unit 158.

The measurement information storage unit 152 stores the biometric information of the worker 5 input from the measurement unit 110. Each piece of the biometric information of the worker 5 and each piece of the environmental information stored in the measurement information storage unit 152 are recorded so that each piece of information at least at the same or near time point can be referred to in association with each other.

The worker information storage unit 154 stores the worker information of the worker 5 input from the authentication unit 130. The worker information of the worker 5 stored in the worker information storage unit 154 is stored in association with at least the time point when the worker 5 is authenticated.

The determination condition storage unit 156 stores determination conditions for determining the safety level of the worker. FIG. 7 is a diagram illustrating an example of a safety level determination condition. The safety level determination condition may be, for example, a stepwise range and a safety level associated with each piece of biometric information and each piece of environmental information. In addition, the safety level determination condition may be, for example, a safety level associated with a determination by a conditional expression that combines a plurality of pieces of biometric information or environmental information in a complex manner (for example, a safety level 2 may be set in a case where a body temperature is 37° C. or more and less than 37.5° C. and a temperature is 32° C. or more). As the safety level determination condition, different conditions may be set for each attribute of the worker. For example, different safety level determination conditions may be prepared for each predetermined age range. In addition, as the safety level determination condition, different conditions may be set for each worker.

The safety level determination unit 158 determines the current safety level on the basis of the biometric information of the worker 5 and the environmental information stored in the measurement information storage unit 152, the worker information stored in the worker information storage unit 154, and the safety level determination condition stored in the determination condition storage unit 156 and outputs the current safety level to the control unit 170. The safety level determination unit 158 may determine the current safety level by applying at least the latest biometric information and environmental information stored in the measurement information storage unit 152 to the safety level determination condition stored in the determination condition storage unit 156. In a case where the safety level determination condition stored in the determination condition storage unit 156 is set for each worker attribute, the safety level determination unit 158 acquires the attribute of the worker 5 by referring to the current worker information of the worker 5 stored in the worker information storage unit 154 and determines the safety level by using the safety level determination condition applied to the attribute.

The safety level determination unit 158 may be allowed to determine the safety level every predetermined period. The safety level determination unit 158 stores the determination result of the safety level for a predetermined time interval, and even in a case where the safety level increases as a result of the determination based on the safety level determination condition, the safety level may not be determined to have increased until a predetermined safety grace period $T_g$ has elapsed after the decrease of the safety level. This is intended to prevent the work restriction from being released easily in a case where the situation seems to be improved due to the temporary change of the biometric information and the environmental information for some reason.

The control unit 170 is realized by executing the system program read from the ROM 12 by the CPU 11 included in the controller 1 illustrated in FIG. 1 and mainly allowing the CPU 11 to perform the arithmetic processing using the RAM 13 and the non-volatile memory 14, the input/output processing using the interfaces 17 and 18, the control processing using the interface 19, and the like. The control unit 170 controls the industrial machine 2 which is restricted on the basis of the determined safety level.

The control unit 170 includes a drive restriction unit 171, a safety function activation unit 172, a machine control unit 174, a manipulation input unit 176, and a display unit 178.

The drive restriction unit 171 first imposes a restriction on the operation of the industrial machine 2 according to the safety level determined by the safety level determination unit 158. Then, the drive restriction unit 171 instructs the machine control unit 174 to perform control of the operation of the industrial machine 2 on the basis of the control program stored in the memory and the manipulation by the worker 5 input from the input device 71 such as a manipulation panel. The manipulation input from the input device 71 by the worker 5 may be allowed to be input to the drive restriction unit 171 by the manipulation input unit 176. The restriction imposed on the operation of the industrial machine 2 by the drive restriction unit 171 differs depending on the type of the industrial machine 2. For example, in a case were the industrial machine 2 is a machine tool or a robot that processes a workpiece by relatively moving the tool and the workpiece, the drive restriction unit 171 may be allowed to restrict the moving speed of the shaft by reducing an override value according to the safety level. By imposing such a restriction, even in a case where the worker 5 generates heat and cannot concentrate, the industrial machine 2 is allowed to operate slowly according to the state, so that the operation of the industrial machine 2 cannot be uncontrollable and dangerous. For example, the drive restriction unit 171 may be allowed to restrict the movable range according to the safety level in a case where the industrial machine 2 is a robot. By imposing such a restriction, even in a case where the worker 5 is swaying his/her feet, an operation range of the industrial machine 2 is restricted in accordance with the state. For this reason, there is no danger that the industrial machine 2 hits the worker 5 and becomes dangerous. The drive restriction by the drive restriction unit 171 may be displayed on the display device 70 by the display unit 178.

The safety function activation unit 172 first imposes a restriction on the operation of the industrial machine 2 by activating the safety function according to the safety level determined by the safety level determination unit 158. Then, the safety function activation unit 172 instructs the machine control unit 174 to perform control of the operation of the industrial machine 2 on the basis of a control program 200 and the manipulation by the worker 5 input from the input device 71 such as a manipulation panel. The manipulation input from the input device 71 by the worker 5 may be allowed to be input to the drive restriction unit 171 by the manipulation input unit 176. The type of safety function activated by the safety function activation unit 172 differs depending on the type of the industrial machine 2. For example, in a case where the industrial machine 2 is a machine tool or a robot that processes a workpiece by relatively moving the tool and the workpiece, the safety function activation unit 172 may be allowed to activate the safety function of monitoring the operation speed of the machine tool or the robot and raising an alert according to the safety level. For example, in a case where the industrial machine 2 is a robot, the safety function activation unit 172 may allowed to activate the safety function of monitoring a movable position of the robot and raising an alert according to the safety level. The activation of the safety function by the safety function activation unit 172 may be allowed to be displayed on the display device 70 by the display unit 178.

FIG. 9 is a diagram illustrating the restriction according to the safety level by the drive restriction unit 171 and the safety function activation unit 172. As illustrated in FIG. 9, the drive restriction unit 171 and the safety function activation unit 172 may be configured to change the restriction stepwise according to the safety level determined by the safety level determination unit 158. In a case where the predetermined safety level is determined, the drive restriction unit 171 and the safety function activation unit 172 instructs the machine control unit 174 to control the operation of the industrial machine 2 in a state where a predetermined drive restriction and the activation of the safety function are performed without stopping the operation of the industrial machine 2. In a case where the safety level in the normal state is determined, the drive restriction unit 171 and the safety function activation unit 172 may be allowed not to restrict the drive, and furthermore, to stop the safety function. In addition, the drive restriction unit 171 and the safety function activation unit 172 may be allowed to perform the drive restriction such as stopping the operation of the industrial machine 2 and the activation of the safety function only in a case where the safety level in the most dangerous state is determined.

The machine control unit 174 controls the operation of the industrial machine 2. The machine control unit 174 has a function of controlling a general industrial machine 2. For example, the machine control unit 174 controls the movement amount of each motor of the industrial machine 2 on the basis of the movement instruction to the motors provided in the industrial machine 2. In addition, the machine control unit 174 performs control of peripheral devices included in the industrial machine 2.

The controller 1 according to the embodiment having the above-described configuration determines the safety level according to the current situation of the worker 5 on the basis of the biometric information of the worker 5 and the environmental information. Then, while performing the drive restriction of the industrial machine 2 and the activation of the safety function on the basis of the determined safety level, the controller performs control of the industrial machine 2.

By using the controller 1 according to the embodiment, even in a case where the situation of the worker 5 deteriorates, if the work can be continued by restricting the operation of the industrial machine 2, the work can be continued within the range of the restriction. For this reason, it is possible to continue the work without suddenly reducing the production efficiency and with actively reducing the risk of manipulation error or accident occurrence.

Figure 10:
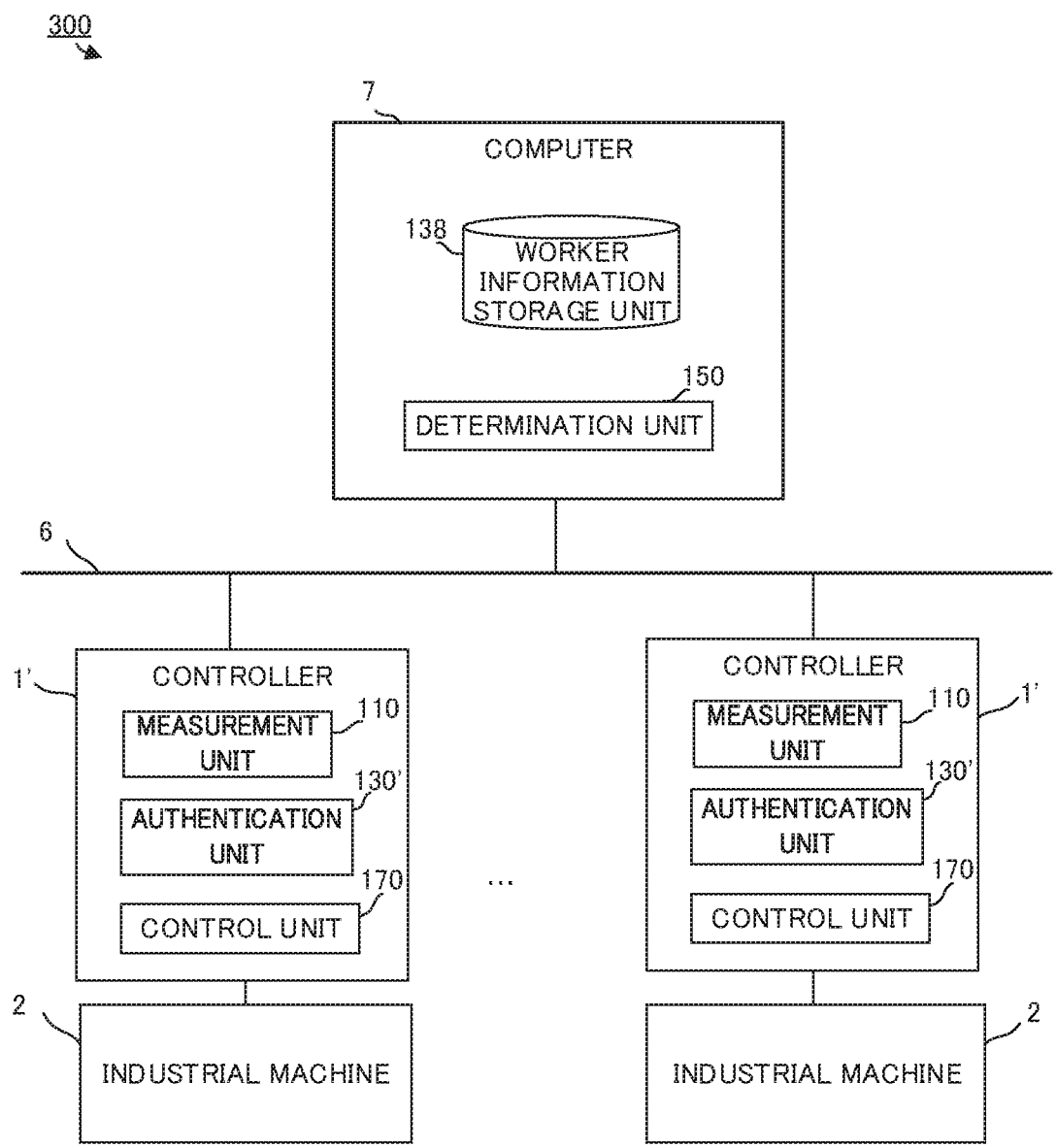
FIG. 10 is a schematic hardware configuration diagram of a control system according to a second embodiment.

FIG. 10 is a block diagram illustrating a schematic function of a control system 300 according to a second embodiment. In the control system 300 according to the embodiment, the worker information storage unit 138 and the determination unit 150 included in the controller 1 described in the first embodiment are provided on a computer 7 such as a fog computer or a cloud server. Then, the control system 300 is configured by connecting the computer 7, a measurement unit 110, an authentication unit 130' (which does not include the worker information storage unit 138), and a controller 1' including a control unit 170 via a wired/wireless network 6. Data exchange is performed between each function of the controller 1' and the worker information storage unit 138 and the determination unit 150 included in the computer 7 via the network 6.

The control system 300 according to the embodiment can share the worker information stored in the worker information storage unit 138 and the determination unit 150 among the plurality of controllers 1'. For this reason, the memory capacity of each controller 1' can be reduced. In addition, since the computer 7 has only to be changed when modifying the worker information, the safety level determination conditions, and the like, maintenance costs can be suppressed.

Although the embodiments have been described above, the application is not limited to only the examples of the above-described embodiments and can be implemented in various modes by making appropriate changes.

The invention claimed is:

1. A control system configured by connecting a controller controlling an industrial machine and a computer via a network, the control system comprising:
    a biometric information acquisition unit acquiring biometric information of a worker;
    an environmental information acquisition unit acquiring environmental information related to a work environment of the worker;
    a determination condition storage unit storing a safety level determination condition as a condition for determining a safety level of the worker on a basis of the biometric information and the environmental information and being set according to an attribute of the worker that uniquely identifies the worker;
    a safety level determination unit determining the safety level of the worker based on the biometric information of the worker, the environmental information, authentication information of the user, and the safety level determination condition stored in the determination condition storage unit;
    a drive restriction unit continuing an operation of the industrial machine in a state of a predetermined restriction being applied to a driving unit of the industrial machine on the basis of the safety level determined by the safety level determination unit; and
    a safety function activation unit continuing the operation of the industrial machine in a state of a predetermined safety function being activated on the basis of the safety level determined by the safety level determination unit, wherein the predetermined safety function monitors either of an operation speed and a movable position of the industrial machine and provides an instruction for the controller controlling the operation to correspond to the determined safety level of the worker.

2. A controller controlling an industrial machine, the controller comprising:
    a biometric information acquisition unit acquiring biometric information of a worker;
    an environmental information acquisition unit acquiring environmental information related to a work environment of the worker;
    a determination condition storage unit storing a safety level determination condition as a condition for determining a safety level of the worker on a basis of the biometric information and the environmental information and being set according to an attribute of the worker that uniquely identifies the worker;
    a safety level determination unit determining the safety level of the worker based on the biometric information of the worker, the environmental information, authentication information of the user, and the safety level determination condition stored in the determination condition storage unit;
    a drive restriction unit continuing an operation of the industrial machine in a state of a predetermined restriction being applied to a driving unit of the industrial machine on the basis of the safety level determined by the safety level determination unit; and
    a safety function activation unit continuing the operation of the industrial machine in a state of a predetermined safety function being activated on the basis of the safety level determined by the safety level determination unit, wherein the predetermined safety function monitors either of an operation speed and a movable position of the industrial machine and provides an instruction for the controlling the operation to correspond to the determined safety level of the worker.

3. The controller according to claim 2, further comprising a worker identification unit acquiring the worker identification information of the worker,
    wherein the safety level determination condition is set for each of the identified workers.

* * * * *